United States Patent
Fujii

(10) Patent No.: US 6,545,125 B1
(45) Date of Patent: Apr. 8, 2003

(54) COMPOUNDS WITH ANTITUMOR ACTIVITY

(75) Inventor: Nobutaka Fujii, Shiga (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/554,706

(22) PCT Filed: Nov. 18, 1998

(86) PCT No.: PCT/JP98/05172

§ 371 (c)(1),
(2), (4) Date: May 18, 2000

(87) PCT Pub. No.: WO99/25729

PCT Pub. Date: May 27, 1999

(30) Foreign Application Priority Data

Nov. 18, 1997 (JP) .............................................. 9-356025

(51) Int. Cl.[7] .............................................. A61K 38/04
(52) U.S. Cl. ........................ 530/329; 530/317; 530/345; 514/2; 514/11; 514/16
(58) Field of Search ................................ 530/329, 317, 530/345; 514/2, 16, 11

(56) References Cited

PUBLICATIONS

Nagy, et al., "Design, Synthesis and in vitro Evaluation of Cytotoxic Analogs of bombesin–like Peptides Containing Doxorubicin or its Intensely Potent Derivative, 2–pyrrolinodoxorubicin," *Proc. Natl. Acad. Sci. USA* 94:652–656 (1997).

Nagy, et al., "Selective Coupling of Methotrexate to Peptide Hormone Carriers Through a γ–carboxamide Linkage of its Glutamic Acid Moiey: Benzotriazol–1–yloxytris(dimethylamino)phosphonium hexafluorophosphate Activation in Salt Coupling," *Proc. Natl. Acad. Sci. USA* 90:6373–6376 (1993).

*Primary Examiner*—Christopher S. F. Low
*Assistant Examiner*—David Lukton
(74) *Attorney, Agent, or Firm*—Browdy and Neimark

(57) ABSTRACT

Compounds of the formula (1) or tautomers, stereoisomers or optical isomers thereof of the formula

X—L—Y wherein X is paclitaxel or its derivative; L represents a linker having at least one functional group; and Y represents 20 Claims, 1 Drawing Sheet

COMPOUNDS WITH ANTITUMOR ACTIVITY

CROSS REFERENCE TO RELATED APPLICATION

The present application is the national stage under 35 U.S.C. 371 PCT/JP98/05172, filed Nov. 18, 1998.

TECHNICAL FIELD

This invention relates to conjugates which are useful in treating cancer and anticancer agents containing these conjugates as the active ingredient.

BACKGROUND ART

It is known that taxols such as docetaxel and paclitaxel inhibit cell proliferation based on the effects of promoting tubulin polymerization and stabilizing microtubules, thereby showing antitumor activity. Owing to these characteristics, taxols are expected to be useful as anticancer agents with a novel function mechanism. In particular, attempts have been made to clinically apply taxols to remedies for mammary cancer, ovarian cancer and nonsmall cell lung cancer (K. C. Nicolau, Nature, 367, 630 (1994); R. A. Holton, J. Am. Chem. Soc., 116, 1587 (1994); D. Masopaolo, A. Camerman, Y. Luo, G. D. Brayer & N. Camerman, Proc. Natl. Acad. Sci. USA, 92, 6920 (1995); Gan to Kagakuryhoho (Cancer and Chemotherapy) 21(5), 583 (1994)).

However, these compounds are poor in solubility and thus studies are in progress both in Japan and abroad to overcome this problem.

On the other hand, it is known that many tumor cells show overexpression of somatostatin receptor (Y. Yamada & S. Kiyono, Saibo Kogaku (Cell Technology), 12(9), 665 (1993); S. Kiyono & Y. Yamada, Naibunpitsugaku no Shinpo (Advances in Endocrinology), 10, 41 (1992)). It is also known that somatostatin derivatives such as octreotide show antitumor activity via the activity of inhibiting tyrosine kinase. In particular, Keri et al. recently reported a tumor cell-specific derivative TT232 (Gy. Keri, et al., Biochem. Biophys. Res. Comm., 191, 681(1993); Gy. Keri, et al., Peptide Research, 6, 281(1993); Gy. Keri, et al., (1993), Peptide Chemistry 1992, ed. N. Yanaihara (Leiden:ESCOM Science Publishers B.V.) pp. 334–336; Gy. Keri, et al., Proc. Natl. Acad. Sci. USA, 93, 12513 (1996)).

Moreover, bombesin-like peptides (GRP; gastrin releasing peptide, NM-C; neuromedin C) have been identified as autocrine growth factors of small cell lung cancer (SCLC) and it is known that receptors of these peptides are overexpressed on SCLC. Accordingly, it is expected that efficacious bombesin antagonists might be useful as anticancer agents specific to SCLC (F. Cuttina, Nature, 316, 823 (1985); D. H. Coy, J. Biol. Chem., 264, 14691 (1989); L. H. Wang, Biochemistry, 29, 616 (1990); D. H. Coy, Eur. J. Pharmacol., 190, 31 (1990)). The present inventors synthesized EABI [(E)-alkene-bombesin isostere] which contains an (E)-alkene type dipeptide Isostere (N. Fujii, Tetrahedron Lett., 32, 4969 (1991); N. Fujii, J. Chem. Soc., Perkin I, 1995, 1359) and clarified that this substance shows a potent antagonism in the amylase secretion system (M. Wada, Pancreas, 10, 301 (1995); N. Fujii, Peptides 1994, ed. H. L. S. Maia, Escom Science Publishers B.V. (1995), pp. 77–78; K. Fujimoto, Life Sciences, 60, 29 (1997)). In these days, it has been a practice to use cisplatin, carboplatin, etc. as the first-line drugs for SCLC. However, these drugs still suffer from some problems including side effects and the expression of tolerance thereto.

Therefore, it has been further required to develop drugs which are free from the problems encountering in the conventional anticancer agents, for example, short blood half time of peptide antitumor substances and poor solubility of highly efficacious anticancer agents such as paclitaxel derivatives.

DISCLOSURE OF THE INVENTION

An object of the present invention is to provide drugs with antitumor activity which are useful as remedies for cancer such as digestive system cancer, mammary cancer, ovarian cancer, lung cancer, etc., more particularly, anticancer agents comprising conjugates wherein a peptide ligand capable of binding specifically to a receptor expressed specifically in tumor cells is covalently bonded to a paclitaxel derivative via a linker.

As a result of intensive studies to solve the above-described problems, we found that the above problem can be solved by using conjugates and that the conjugates exhibit excellent effects as anticancer agents wherein one or more compounds with antitumor activity are chemically bonded to a peptide or a pseudopeptide having an affinity for a receptor expressed on tumor cells, thereby completing the present invention.

Accordingly, the present invention provides a conjugate wherein one or more compounds with antitumor activity are chemically bonded to a peptide or a pseudopeptide having an affinity for a receptor expressed on tumor cells.

The present invention further provides a compound represented by the following general formula (1) or potential tautomers, stereoisomers or optical isomers thereof:

X—L—Y (wherein X represents paclitaxel or its derivative; L represents a linker having (a) functional group(s); and Y represents TT232: general formula

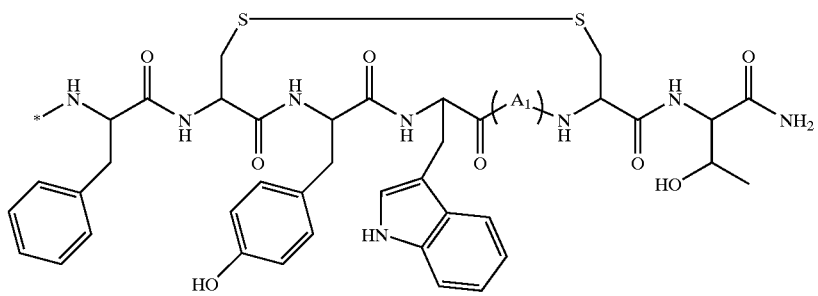

(wherein $A_1$ represents a lysine residue, a citrulline residue, an arginine residue or an ornithine residue; and the amino and carboxyl groups bonded to the α-carbon atom are each bonded to form an amide); or EABI: general formula

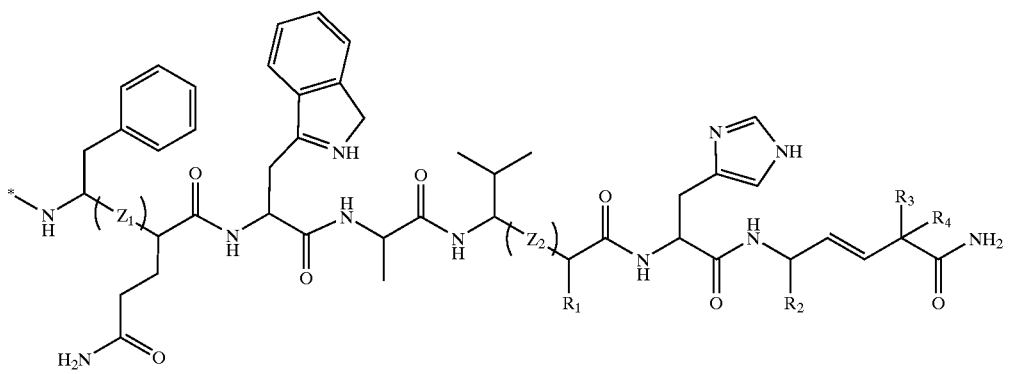

(wherein $Z_1$ represents C(=O)NH or (E)CH=CH; $Z_2$ represents C(=O)NH or (E)CH=CH; $R_1$ represents H or a methyl group; $R_2$ represents an isobutyl group or an isopropyl group; $R_3$ represents H, an isobutyl group or a benzyl group; and $R_4$ represents H or an isobutyl group); and * represents a bond to L.

The present invention further provides a compound represented by the following general formula (1) or potential tautomers, stereoisomers or optical isomers thereof:

X—L—Y (wherein X represents paclitaxel or its derivative; L represents a linker having (a) functional group(s); and Y represents TT232: specific compound 232

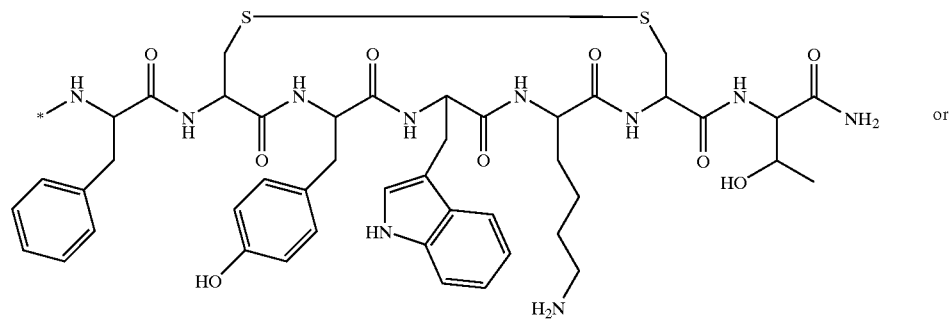

or

EABI: specific compound

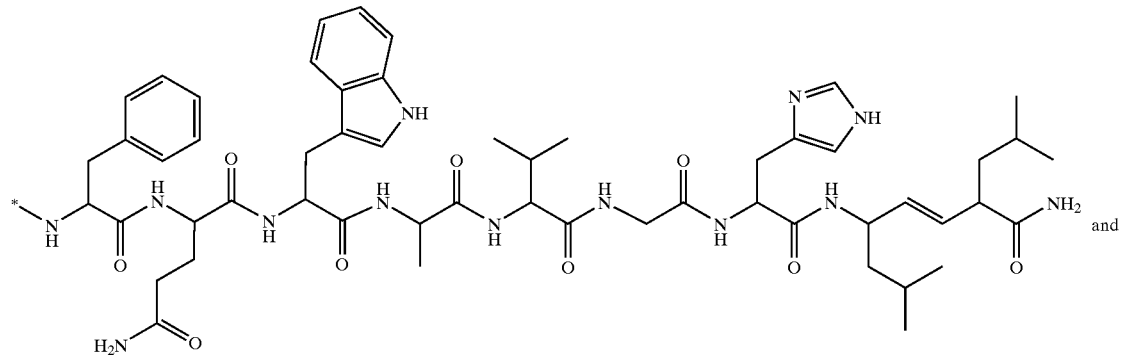

and

* represents a bond to L.

The present invention further provides a compound represented by the following general formula (1) or potential tautomers, stereoisomers or optical isomers thereof:

X—L—Y (wherein X represents paclitaxel or its derivative; L represents a linker having (a) functional group(s); and Y represents a pseudopeptide having an affinity for a receptor expressed on tumor cells. Although the chemical binding manner is not restricted, there may be mentioned, for example, a linker capable of binding both to the peptide or pseudopeptide and the compound with antitumor activity. In this case, it is preferable that one end of the linker can be bonded (for example, via a covalent bond) to the peptide or pseudopeptide while the other end of the linker can be bonded (for example, via a covalent bond) to the compound with anti- TT232: specific compound (optically active)

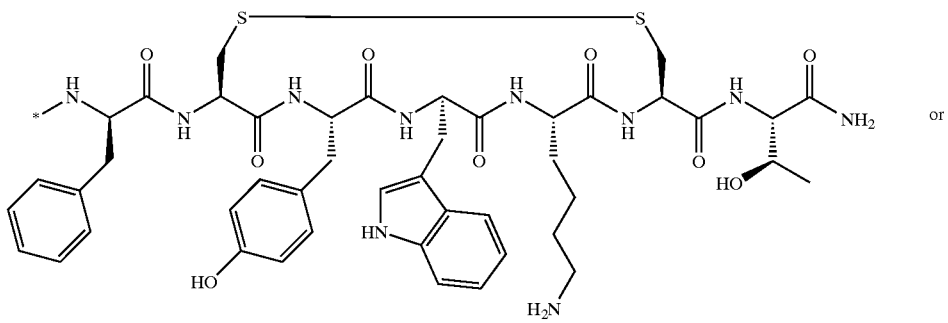

or

EABI: specific compound (optically active)

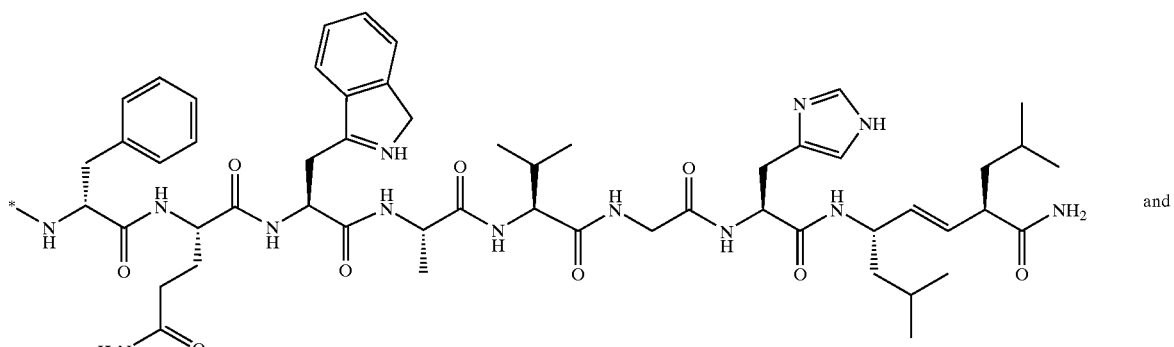

and

* represents a bond to L.

Moreover, the present invention further provides compositions with antitumor activity and anticancer agents which contain the compounds represented by the above general formula (1) or potential tautomers, stereoisomers or optical isomers thereof.

BEST MODE FOR CARRYING OUT THE INVENTION

Figure 1:
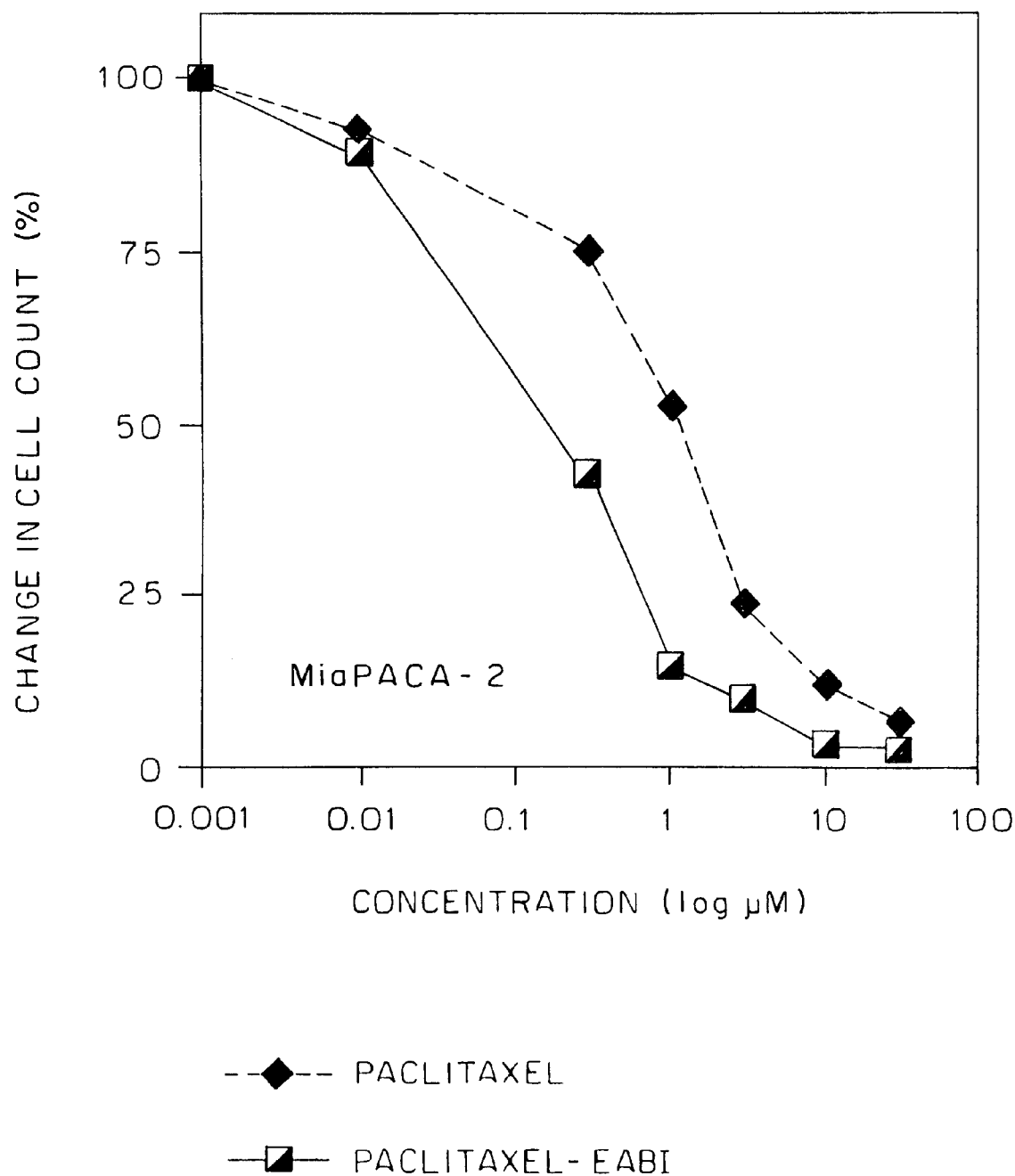
FIG. 1 provides a graph which shows the inhibition of the pancreatic cancer cell proliferation by a paclitaxel-(succinic acid)-EABI conjugate.

In the present invention, the receptor expressed on tumor cells is not restricted in type. Examples thereof include somatostatin receptor and bombesin-like peptides receptors.

The term "a pseudopeptide having an affinity for a receptor expressed on tumor cells" as used herein means one wherein one or more amino acid residues in a peptide have been substituted by structure(s) having a structural homology with peptide bond (for example, (E)-alkene isosteres). Those from which amino acid residue(s) have been deleted also fall within this category.

In the present invention, one or more compounds with antitumor activity are chemically bonded to a peptide or a pseudopeptide having an affinity for a receptor expressed on tumor cells. Although the chemical binding manner is not restricted, there may be mentioned, for example, a linker capable of binding both to the peptide or pseudopeptide and the compound with antitumor activity. In this case, it is preferable that one end of the linker can be bonded (for example, via a covalent bond) to the peptide or pseudopeptide while the other end of the linker can be bonded (for example, via a covalent bond) to the compound with antitumor activity. As a linker of this type, it is possible to use one capable of binding to an amino acid in the peptide or pseudopeptide and to a hydroxyl group in the compound with antitumor activity. Particular examples of such a linker include compounds having two or more carboxyl groups. When a compound having two or more carboxyl groups is used, one carboxyl group forms an amide bond together with an amino acid in the peptide or pseudopeptide, while another carboxyl group forms an ester bond together with a hydroxyl group in the compound with antitumor activity and thus the peptide or pseudopeptide is bonded to the compound with antitumor activity. The compound having two or more carboxyl groups may have other functional groups, so long as the binding of the peptide or pseudopeptide to the compound with antitumor activity is not inhibited thereby. Examples of the compound having two or more carboxyl groups include aromatic compounds, aliphatic open-chain compounds, alicyclic compounds and heterocyclic compounds. Among all, aliphatic open-chain compounds are preferable and dicarboxylic acids (in particular, succinic acid and glutaric acid) are still preferable.

With respect to the definition in the general formula (1), the paclitaxel derivative represented by X may be an arbitrary one selected from among compounds having the baccatin skeleton and publicly known taxol derivatives having antitumor activity. Among all, docetaxel is particularly preferable therefor.

The linker L having a functional group is not particularly restricted, so long as it exerts no undesirable effect on the antitumor activity. As above mentioned linker L, there may be mentioned, for example, —(CO)—A—(CO)— (wherein A represents an optionally substituted alkylene group having 2 to 4 carbon atoms). In this case, examples of the substituent in A (i.e., an optionally substituted alkylene group having 2 to 4 carbon atoms) include linear or branched alkyl groups having 1 to 3 carbon atoms and hydroxyl group.

X and L may be bonded to each other in an arbitrary manner without restriction, so long as the object of the present invention can be achieved. For example, the —CO moiety of the linker L having the structure —(CO)—A—(CO)— may be bonded to the 2'-position of X via an ester bond. Alternatively, the —CO moiety of the above-described linker L may be bonded to the 3'-position of X via an amide bond. It is particularly preferable that the —CO moiety of the linker L is bonded to the 2'-position of X via an ester bond.

Also, L and Y may be bonded to each other in an arbitrary manner without restriction, so long as the object of the present invention can be achieved. For example, the —CO moiety of the linker L having the structure —(CO)—A—(CO)— may be bonded to the NH-moiety of Y via an amide bond. It is particularly preferable that the —CO moiety of the linker L is bonded to the NH-moiety of the Phe (phenylalanine) residue of Y via an amide bond.

Preferable examples of X include paclitaxel and docetaxel.

Preferable examples of A include ethylene and trimethylene groups.

As Y, any group cited in the definition in the general formula (1) is preferable. When Y is represented by the above-described general formula TT232, it is particularly preferable that $A_1$ is a lysine residue. When Y is represented by the above-described general formula EABI, it is particularly preferable that $Z_1$ is C(=O)NH, $Z_2$ is C(=O)NH, $R_1$ is H, $R_2$ is an isobutyl group, and one of $R_3$ and $R_4$ is an isobutyl group while the other is H.

Preferable examples of the compounds represented by the general formula (1) include those having the following structural formulae:

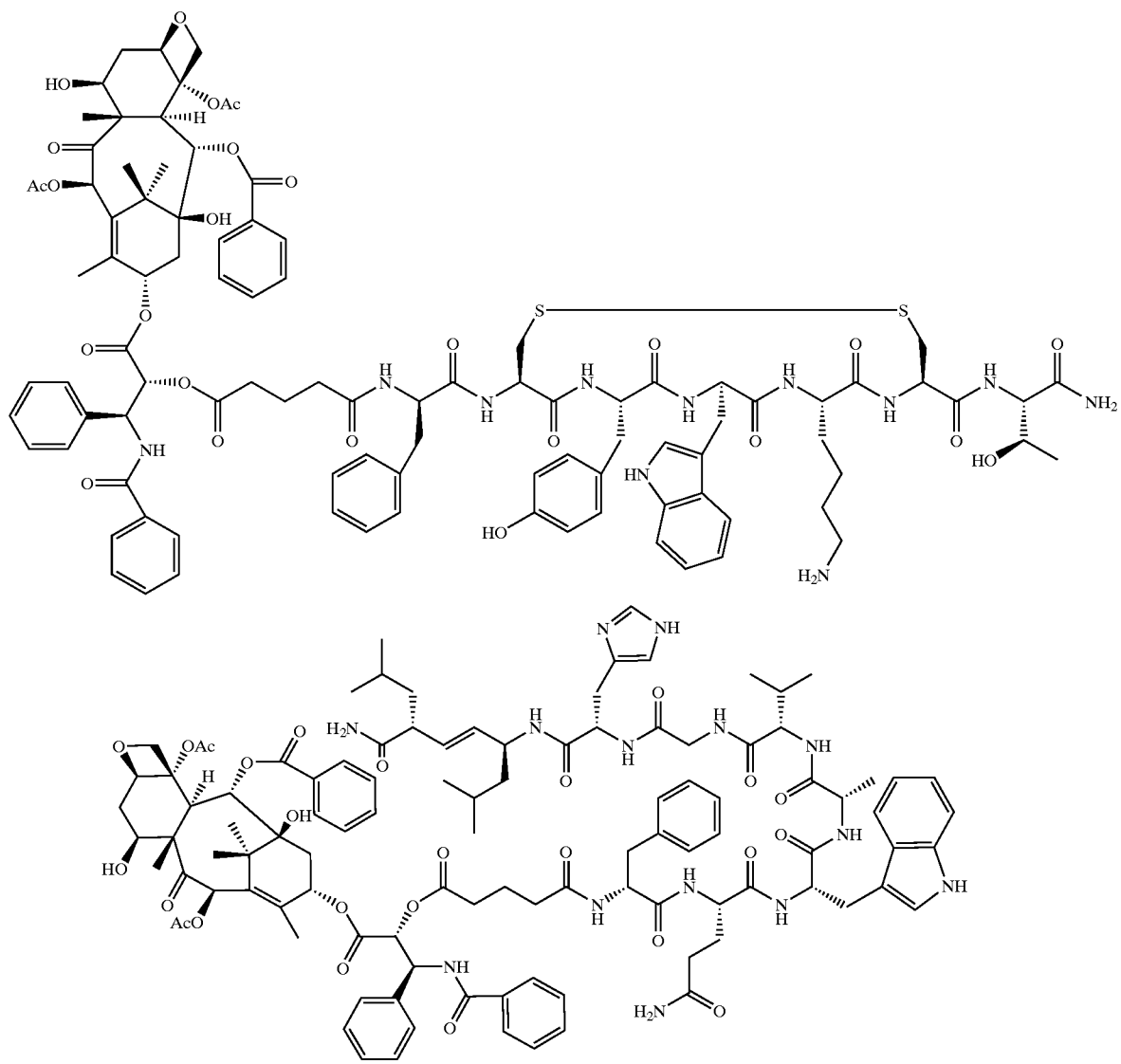

-continued

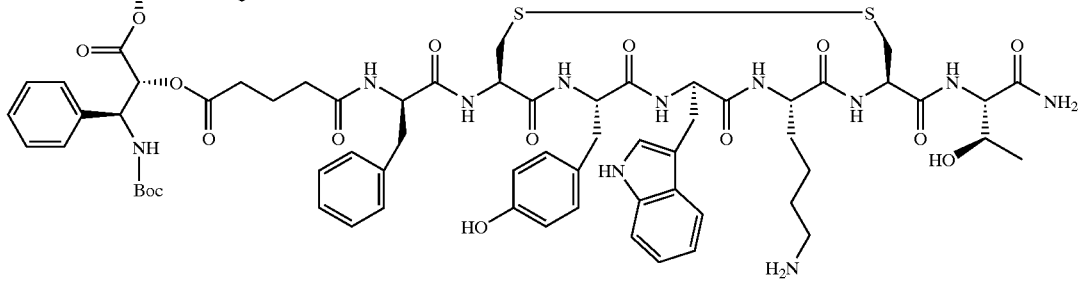

(wherein Boc represents a t-butoxycarbonyl group); and

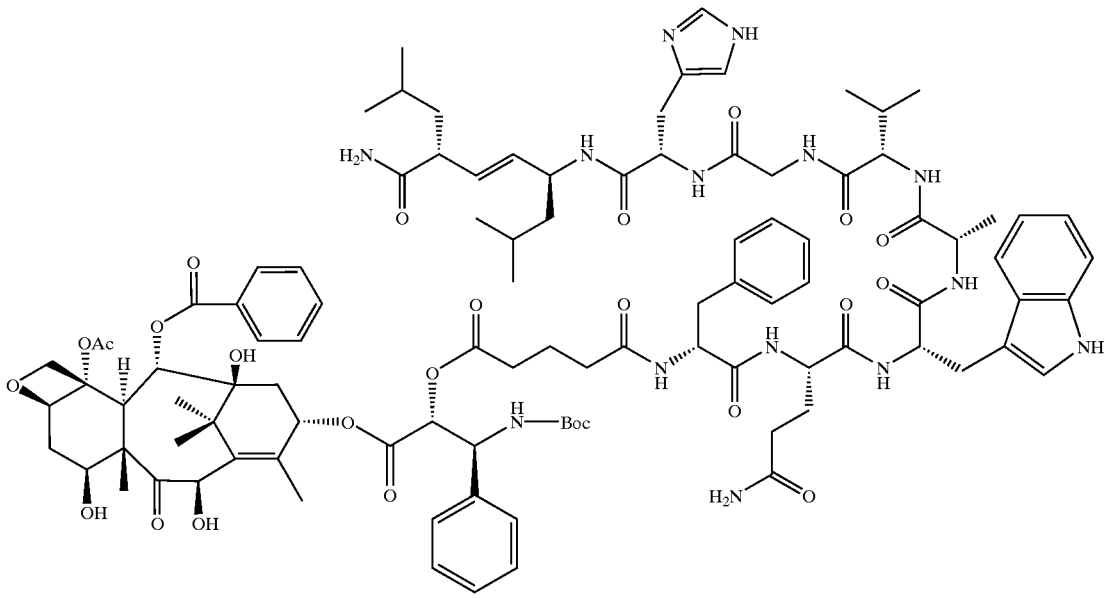

(wherein Boc represents a t-butoxycarbonyl group).

In the present invention, the compounds represented by the general formula (1) involve these compounds per se as well as the potential tautomers, stereoisomers and optical isomers thereof and mixtures of the same.

The conjugate according to the present invention, wherein one or more compounds with antitumor activity are chemically bonded to a peptide or a pseudopeptide having an affinity for a receptor expressed on tumor cells, can be synthesized, for example, by the following method wherein a compound of general formula (1) is employed.

First, the above-described peptide or pseudopeptide is bonded to a linker. For example, paclitaxel is reacted with succinic anhydride in the presence of pyridine to give a paclitaxel-linker bond-structure wherein succinic anhydride is bonded via an ester bond to paclitaxel. Next, the thus obtained paclitaxel-linker bond-structure is condensed with EABI by, for example, the WSCDI-HOBt method to give the aimed paclitaxel-(linker)-EABI conjugate.

The production process as described above will be illustrated by the following chemical formulae:

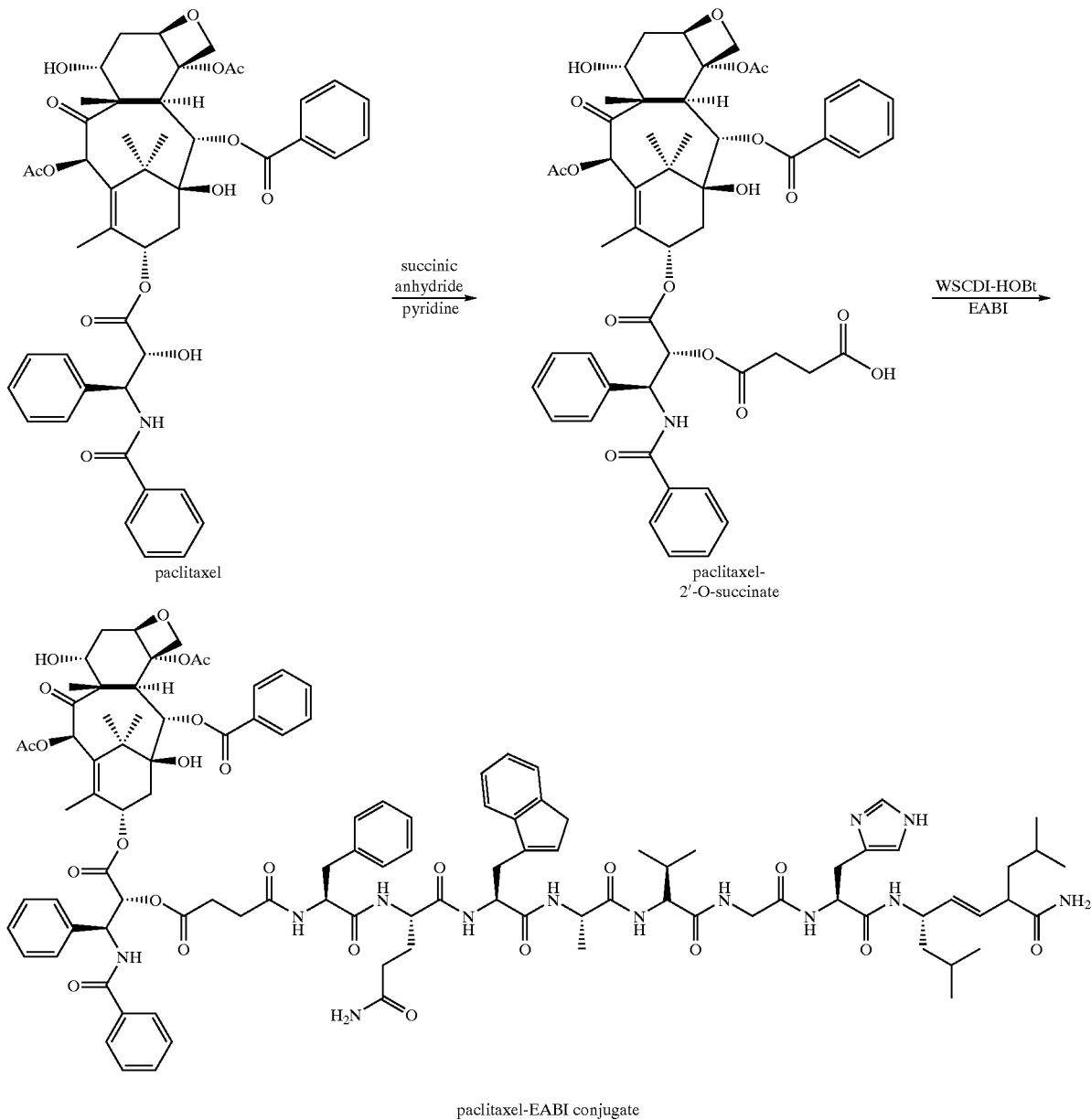

paclitaxel-EABI conjugate

Note:
WSCDI: water soluble carbodiimide.
HOBt: 1-hydroxybenzotriazole hydrate.

Although the production process of a conjugate by using paclitaxel, succinic anhydride and EABI is described above, the conjugates according to the present invention can be synthesized in the same manner by using other combinations. For example, conjugates of the following combinations can be produced by the above-described method.

(1) Paclitaxel-succinic anhydride-TT232.
(2) Paclitaxel-glutaric anhydride-EABI.
(3) Paclitaxel-glutaric anhydride-TT232.
(4) Docetaxel-succinic anhydride-EABI.
(5) Docetaxel-succinic anhydride-TT232.
(6) Docetaxel-glutaric anhydride-EABI.
(7) Docetaxel-glutaric anhydride-TT232.

The paclitaxel or its derivative in the general formula (1) can be obtained by a publicly known method adequate for the desired derivative. For example, paclitaxel can be obtained by the method reported by Kingston, D. G. I., Pharmacol. Ther., 52, 1(1992) and the method disclosed in R. A. Holton, European Patent A 400971,1990. On the other hand, docetaxel can be obtained by the method disclosed in Japanese Patent Application Disclosure SHO No. 63–30479 and the method reported by Greene, A. E. et al., J. Org. Chem., 59, 1238 (1994).

The peptide or pseudopeptide to be used in the present invention can be obtained by applying publicly known methods for synthesizing peptides, for example, the method of N. Fujii et al. (Tetrahedron Lett., 32, 4969 (1991); J. Chem. Soc., Perkin I, 1995, 1359). It is also possible to obtain the peptide or pseudopeptide via the expression in host cells with the use of publicly known gene recombination techniques.

The compounds represented by the general formula (1) may be processed into pharmaceutical compositions, which contain one or more pharmaceutically acceptable diluents, humectants, emulsifiers, dispersants, auxiliary agents, preservatives, buffers, binders, stabilizers, etc., in arbitrary forms appropriate for the desired administration route. Parenteral administration, in particular, intravenous administration is preferable. In the case of parenteral administration, the compositions may be in the form of nonaqueous solutions, suspensions or emulsions. Aseptic preparations can be obtained by, for example, sterile filtration.

The compounds of the present invention may be administered in an appropriate dose determined depending on the body type, age and conditions of the patient, severity of the disease, time after the onset of the disease, etc. In the case of intravenous administration (in particular, drip infusion), paclitaxel or its derivative (for example, docetaxel) is generally given in an amount of 0.1 to 2 mg/kg.

EXAMPLES

Production of the compounds of the present invention will be described in greater detail by reference to the following Examples, but it should be understood that the invention is not construed as being limited thereto.

To exhibit the usefulness of the present invention, the results of Test Example showing the excellent antitumor activity of the compound of the general formula (1) will be also given.

Example 1

1. Synthesis of paclitaxel-succinic acid

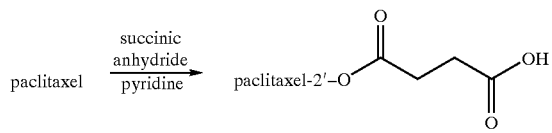

Paclitaxel (50 mg, 1 equivalent) was introduced into a 50 ml round bottomed flask and dissolved in pyridine (3 ml). Next, succinic anhydride (30 mg, 5.1 equivalents) was added thereto. After stirring at room temperature for 16 hours, the mixture was diluted with 30% MeCN (30 ml). Then it was filtered and purified by high performance liquid chromatography (HPLC). After freeze-drying, paclitaxel-succinic acid (51.86 mg, yield 92.2%) was obtained.

$[\alpha]^{23}_D$: −45.11 (c=0.652, 50% MeCN).

MS(FAB)m/z: (calculated as $C_{51}H_{56}NO_7$) (MH$^+$) 954.3547 (found) 954.3574.

2. Synthesis of paclitaxel-(succinic acid)-EABI

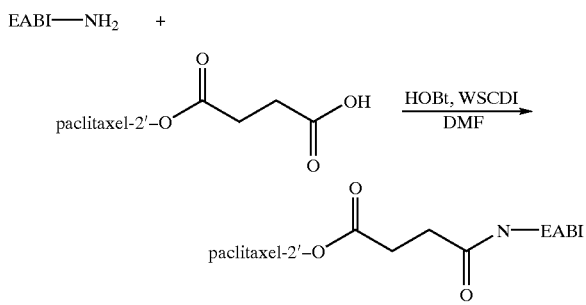

Note:
DMF: N,N-dimethylformamide.

EABI (4.5 mg) was introduced into a 30 ml round bottomed flask and dissolved in 80% MeCN (2 ml). Next, HOBt/DMF (21.8 mg of HOBt dissolved in 50 μl of DMF) was added thereto. After adding paclitaxel-succinic acid (5 mg, 1 equivalent) dissolved in MeCN (100 μl), WSCDI (16.3 μl, 20 equivalents) was further added thereto under ice-cooling. After stirring at room temperature for 2 hours, the mixture was diluted with 30% MeCN (15 ml). Then it was filtered and purified by HPLC. After freeze-drying, paclitaxel-(succinic acid)-EABI (5.68 mg, yield 60.1%) was obtained.

$[\alpha]^{23}_D$: −28.40 (c=0.122, 50% MeCN).

MS(API)m/z: (calculated as $C_{105}H_{131}N_{14}O_{25}$) 1987.9408 (MH$^+$) (found) 1988.5.

Test Example

Test Example 1

By using the paclitaxel-(succinic acid)-EABI conjugate prepared in Example 1, the activity on pancreatic cancer—origin cells was evaluated in the following manner.

Pancreatic cancer-origin cells (cell line: MiaPACA), which had been incubated for 2 days, were brought into contact for 2 hours with the compound of Example 1 at various concentrations. Then, the cells were incubated in a $CO_2$ incubator at 37° C. for 48 hours and viable cells were counted. By using paclitaxel as a control compound, the above procedure was repeated.

FIG. 1 shows the results. As FIG. 1 shows, the paclitaxel-(succinic acid)-EABI conjugate of the present invention shows an antitumor activity comparable to paclitaxel or even exceeding the same. This fact indicates that an anticancer agent can be targeted specifically for tumor cells wherein GRP receptor is expressed.

Industrial Applicability

In the compounds according to the present invention, the problem of short blood half time encountering in the conventional peptide antitumor substances can be overcome. At the same time, these compounds of the present invention sustain the advantages (i.e., little side effects, high affinity for tumor cells and high solubility in water) of the conventional peptide antitumor substances and show improved solubility of paclitaxel derivatives and high antitumor activity thereof. Owing to these characteristics, the compounds of the present invention are highly useful as anticancer agents.

What is claimed is:

1. A compound which exhibits antitumor activity represented by the following formula (1) or a tautomer or a stereoisomer thereof:

$$X-L-Y \tag{1}$$

wherein

X represents (i) paclitaxel or (ii) a derivative thereof selected from the group consisting of taxol derivatives having antitumor activity;

L represents a linker having at least one functional group; and

Y represents the formula

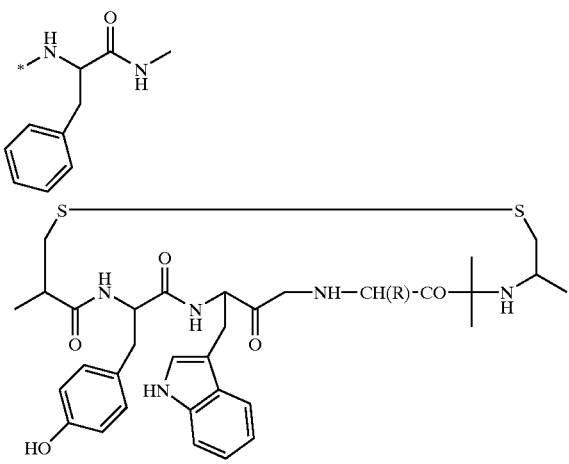

wherein R represents —(CH$_2$)$_4$NH$_2$, —(CH$_2$)$_3$NHCONH$_2$, —(CH$_2$)$_3$NH (C=NH)NH$_2$ or —(CH$_2$)$_3$NH$_2$; or the formula

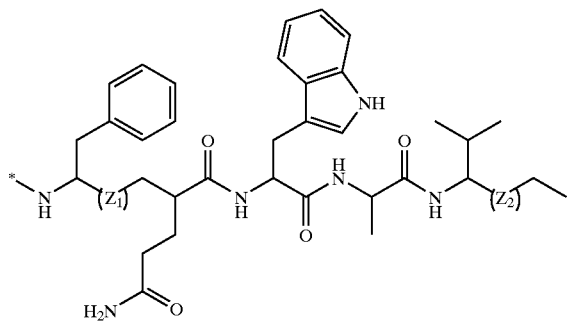

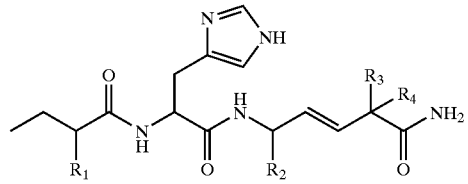

wherein Z$_1$ represents C(=O)NH or (E) CH=CH; Z$_2$ represents C(=O)NH or (E) CH=CH; R$_1$ represents H or a methyl group;

R$_2$ represents an isobutyl group or an isopropyl group;

R$_3$ represents H, an isobutyl group or a benzyl group; and

R$_4$ represents H or an isobutyl group; and

* represents a bond to L.

2. The compound as claimed in claim 1 wherein L is 1,4-dioxobutane or 1,5-dioxopentane.

3. The compound as claimed in claim 2 wherein X is paclitaxel or docetaxel.

4. The compound as claimed in claim 1 wherein X is paclitaxel or docetaxel.

5. An anticancer compound represented by the following formula (1):

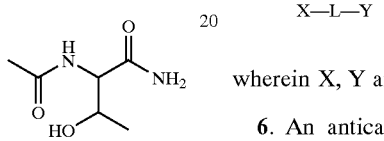

wherein X, Y and L are each defined in claim 1.

6. An anticancer composition comprising at least one compound of the following formula (1):

wherein X, Y and L are each as defined in claim 1, and a pharmaceutically acceptable carrier or diluent.

7. A composition comprising a pharmaceutically acceptable carrier and a compound according to claim 1 in an amount effective to inhibit proliferation of tumor cells.

8. A compound which exhibits antitumor activity represented by the following formula (1) or a tautomer or a stereoisomer thereof:

wherein

X represent (i) paclitaxel or (ii) a derivative thereof selected from the group consisting of taxol derivatives having antitumor activity;

L represents a linker having at least one functional group; and

Y represents the formula

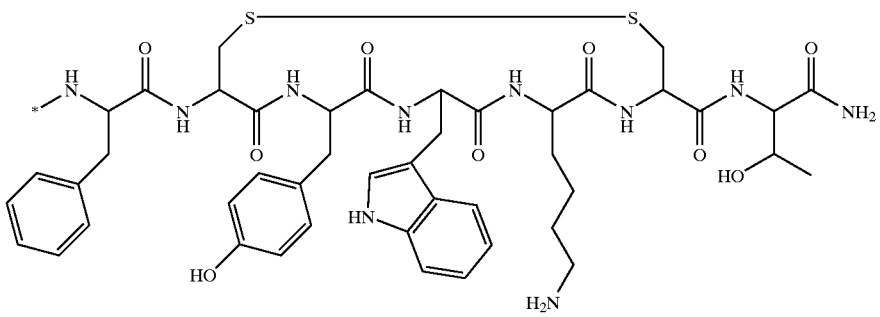

or the formula

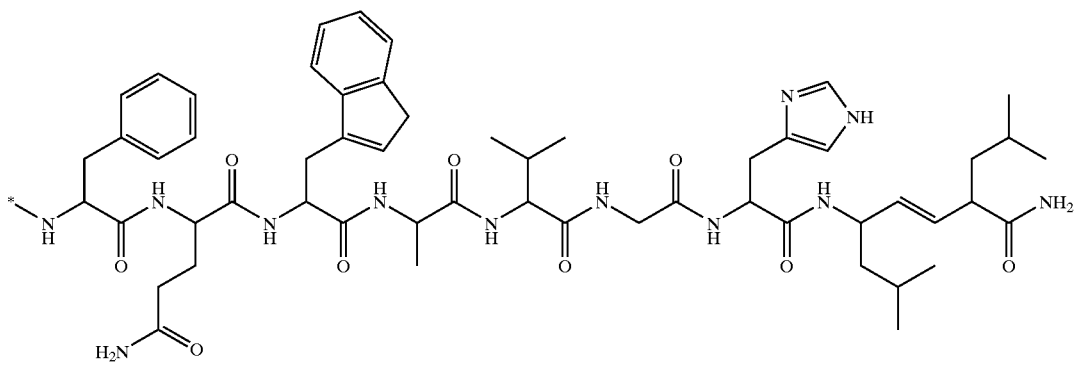

and
*represents a bond to L.

9. The compound as claimed in claim 8 wherein L is 1,4-dioxobutane or 1,5-dioxopentane.

10. An anticancer compound represented by the following formula (1):

X—L—Y       (1)

wherein X, L and Y are each as defined in claim 8.

11. The compound as claimed in claim 8 wherein X is paclitaxel or docetaxel.

12. An anticancer composition comprising at least one compound of the following formula (1):

X—L—Y       (1)

wherein X, Y and L are each as defined in claim 8, and a pharmaceutically acceptable carrier or diluent.

13. A composition comprising a pharmaceutically acceptable carrier and a compound according to claim 8 in an anti-tumor effective amount.

14. A compound which exhibits antitumor activity represented by the following formula (1) or a tautomer or stereoisomer thereof:

X—L—Y       (1)

wherein

X represents (i) paclitaxel or (ii) a derivative thereof selected from the group consisting of taxol derivatives having antitumor activity;

L represents a linker having at least one functional group; and

Y represents the formula

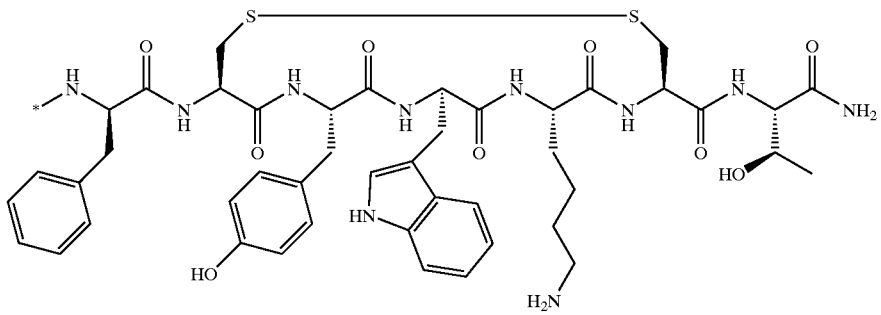

or the formula

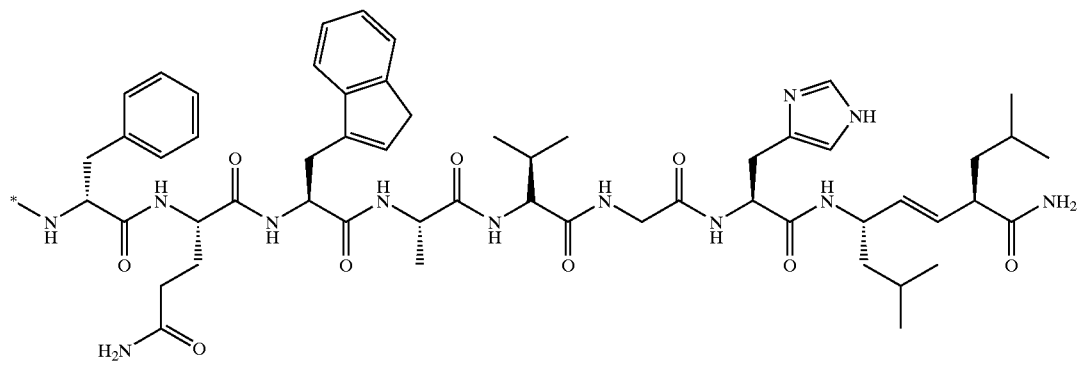

and

*represents a bond to L.

15. The compound as claimed in claim 14 wherein L is 1,4-dioxobutane or 1,5-dioxopentane.

16. The compound as claimed in claim 14 wherein X is paclitaxel or docetaxel.

17. An anticancer compound represented by the following formula (1):

X—L—Y wherein X, L and Y are each as defined in claim 14.

18. A composition comprising a pharmaceutically acceptable carrier and a compound according to claim 14 in an anti-tumor effective amount.

19. An anticancer composition comprising at least one compound of the following formula (1):

X—L—Y    (1)

wherein X, Y and L are each as defined in claim 14, and a pharmaceutically acceptable carrier or diluent.

20. A compound which exhibits antitumor activity selected from the group consisting of those represented by the following structural formulae:

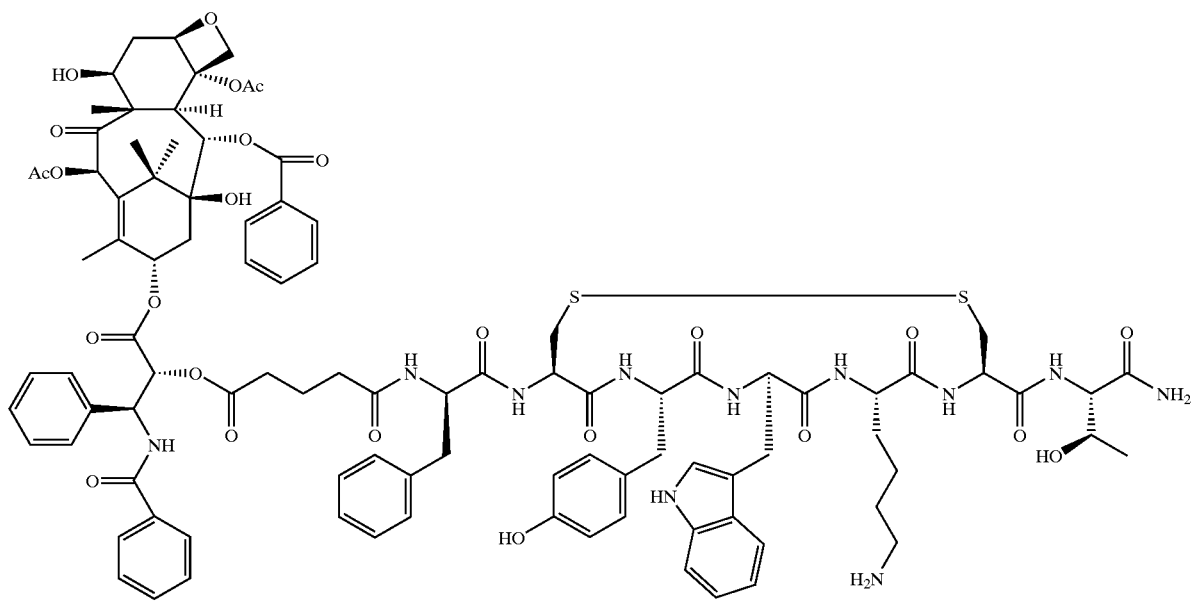

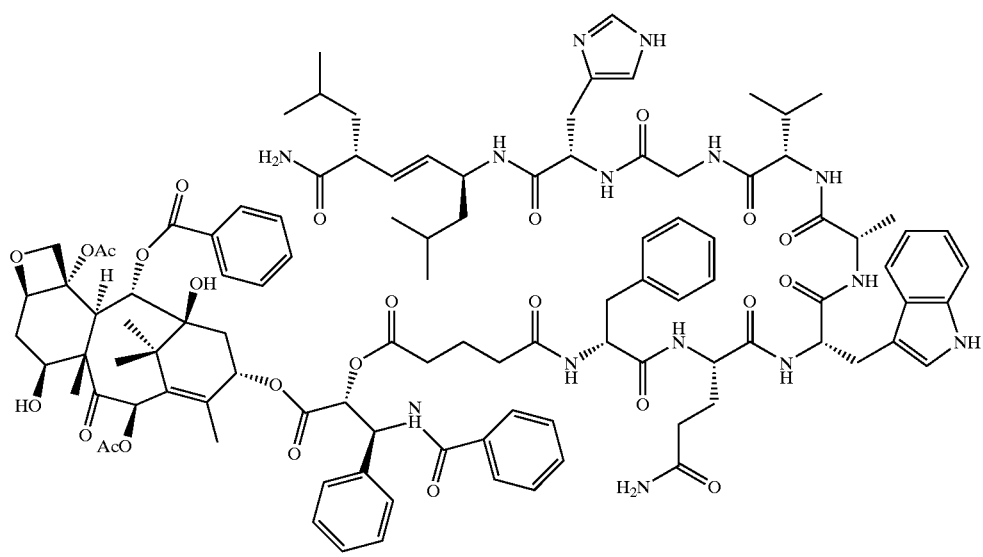

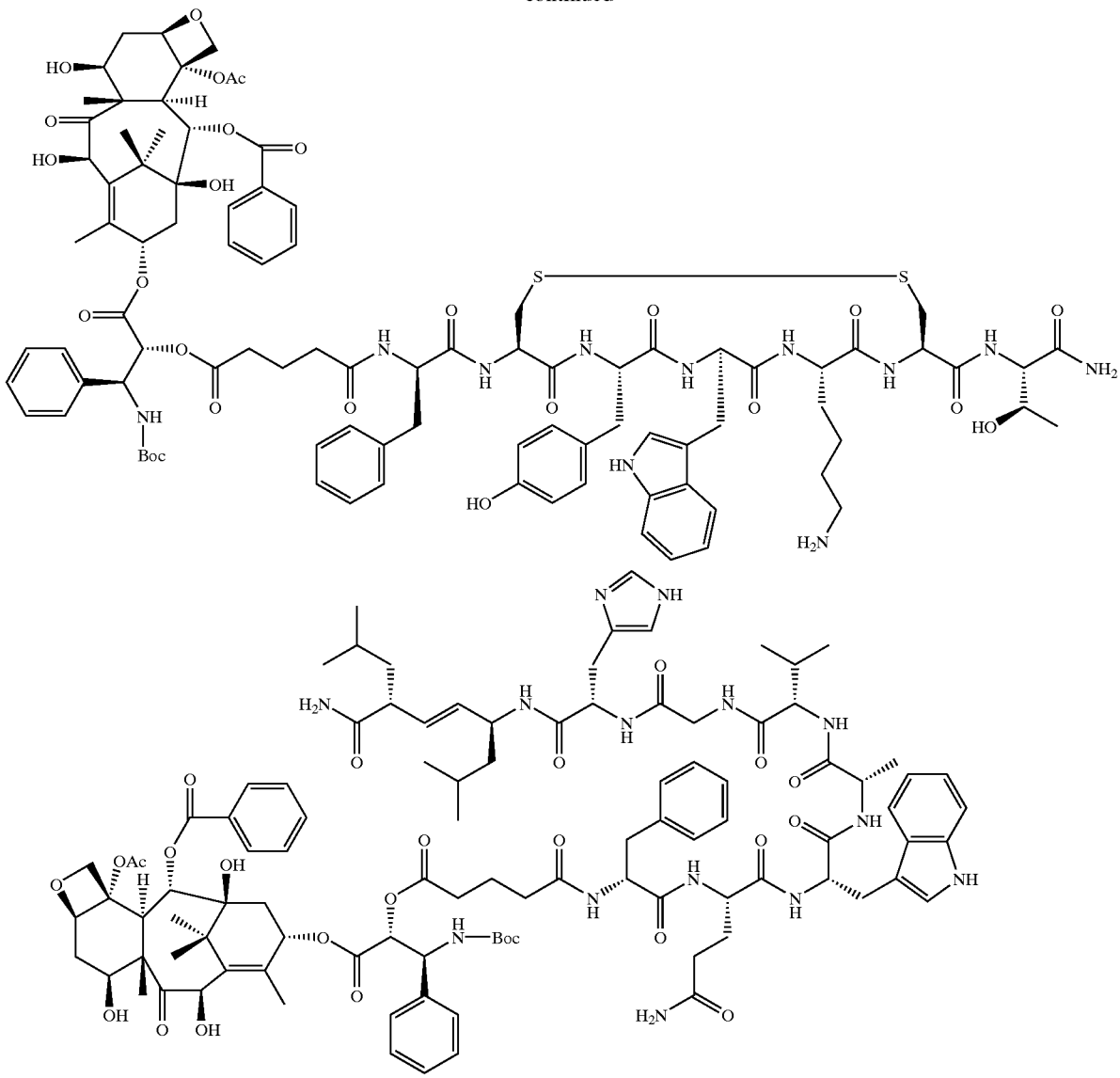
wherein Boc represents a t-butoxycarbonyl group.